United States Patent
Winston et al.

(10) Patent No.: US 6,451,290 B2
(45) Date of Patent: *Sep. 17, 2002

(54) PRODUCTS AND METHODS FOR THE REMINERALIZATION AND PREVENTION OF DEMINERALIZATION OF TEETH

(75) Inventors: Anthony E. Winston, East Brunswick, NJ (US); Norman Usen, Marlboro, NJ (US)

(73) Assignee: Church & Dwight Co., Inc., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/884,354

(22) Filed: Jun. 20, 2001

Related U.S. Application Data

(63) Continuation of application No. 08/722,458, filed on Sep. 27, 1996, now abandoned.

(51) Int. Cl.$^7$ .............................. A61K 9/68; A61K 7/16; A23G 3/30; A23L 1/304
(52) U.S. Cl. .............................. 424/48; 424/440; 426/3; 426/4; 426/5
(58) Field of Search ..................... 424/48, 440; 426/3–5

(56) References Cited

U.S. PATENT DOCUMENTS

| | | |
|---|---|---|
| 1,698,404 A | 1/1929 | Hopkins |
| 2,605,229 A | 7/1952 | Marcus |
| 2,627,493 A | 2/1953 | Merckel et al. |
| 2,700,012 A | 1/1955 | Merckel et al. |
| 3,679,360 A | 7/1972 | Rubin ........................ 23/109 |
| 3,728,446 A | 4/1973 | Roberts et al. ............... 424/49 |
| 3,747,804 A | 7/1973 | Raaf et al. .................... 222/1 |
| 3,913,229 A | 10/1975 | Driskell et al. ............... 32/15 |
| 3,943,267 A | 3/1976 | Randol ......................... 427/2 |
| 3,966,901 A | 6/1976 | Cullum et al. .............. 424/52 |
| 4,048,300 A | 9/1977 | Tomlinson et al. .......... 424/52 |
| 4,075,317 A | 2/1978 | Mitchell et al. ............. 424/52 |
| 4,080,440 A | 3/1978 | DiGiulio ..................... 424/49 |
| 4,083,955 A | 4/1978 | Grabenstetter et al. |
| 4,097,935 A | 7/1978 | Jarcho ........................... 3/1.9 |
| 4,108,980 A | 8/1978 | Duff ............................ 424/52 |
| 4,138,477 A | 2/1979 | Gaffar |
| 4,141,969 A | 2/1979 | Mitchell ...................... 424/52 |
| 4,150,112 A | 4/1979 | Wagenknecht et al. |
| 4,151,270 A | 4/1979 | Ream et al. |
| 4,159,315 A | 6/1979 | Wagenknecht et al. |
| 4,177,258 A | 12/1979 | Gaffar et al. |
| 4,183,915 A | 1/1980 | Gaffar et al. |
| 4,233,288 A | 11/1980 | Cornell |
| 4,244,707 A | 1/1981 | Wason ......................... 51/308 |
| 4,265,877 A | 5/1981 | Tenta |
| 4,280,822 A | 7/1981 | Wason ......................... 51/308 |
| 4,283,385 A | 8/1981 | Dhabbar et al. ............. 424/52 |
| 4,340,584 A | 7/1982 | Wason ......................... 424/52 |
| 4,348,381 A | 9/1982 | Gaffar et al. |
| 4,397,837 A | 8/1983 | Raaf et al. |
| 4,400,372 A | 8/1983 | Muhler et al. |
| 4,405,600 A | 9/1983 | Besic ........................... 424/57 |
| 4,412,983 A | 11/1983 | Mitchell ...................... 424/52 |
| 4,415,550 A | 11/1983 | Pakhomov et al. .......... 424/57 |
| 4,419,341 A | 12/1983 | Kokesnik et al. ............ 424/52 |
| 4,424,203 A | 1/1984 | Pakhomov et al. .......... 424/52 |
| 4,460,565 A | 7/1984 | Weststrate et al. ........... 424/52 |
| 4,474,749 A | 10/1984 | Kruppa |
| 4,487,757 A | 12/1984 | Kiozpeoplou ................ 424/49 |
| 4,515,770 A | 5/1985 | Besic |
| 4,518,430 A | 5/1985 | Brown et al. ................ 106/35 |
| 4,528,180 A | 7/1985 | Schaeffer ..................... 424/52 |
| 4,556,561 A | 12/1985 | Brown et al. .............. 424/151 |
| 4,565,691 A | 1/1986 | Jackson ....................... 424/52 |
| 4,603,045 A | 7/1986 | Smigel ........................ 424/52 |
| 4,606,912 A | 8/1986 | Rudy et al. .................. 424/52 |
| 4,610,873 A | 9/1986 | Rudy et al. .................. 424/52 |
| 4,612,053 A | 9/1986 | Brown et al. |
| 4,672,032 A | 6/1987 | Slavkin et al. ............... 435/68 |
| 4,681,766 A | 7/1987 | Huzinec et al. |
| 4,714,608 A | 12/1987 | Rolla .......................... 424/52 |
| 4,753,790 A | * 6/1988 | Silva et al. .................. 424/48 |
| 4,765,984 A | 8/1988 | Vellekoop et al. |
| 4,786,511 A | 11/1988 | Huzinec et al. |
| 4,812,306 A | 3/1989 | Cockerell et al. ............ 424/52 |

(List continued on next page.)

FOREIGN PATENT DOCUMENTS

| | | |
|---|---|---|
| GB | 1090340 | 3/1965 |
| WO | 9418938 | 9/1994 |

OTHER PUBLICATIONS

International Application Publication WO94/18938, Sep. 1, 1994.

*Primary Examiner*—Shep K. Rose
(74) *Attorney, Agent, or Firm*—Stuart D. Frenkel

(57) ABSTRACT

Improved solid products for remineralizing subsurface lesions and/or mineralizing exposed tubules in dentin contain an anionic component, a cationic component and a separating component for separating the anionic and cationic components in the product. The anionic component contains at least one water-soluble phosphate salt and the cationic component contains at least one partially water-soluble calcium salt. To remineralize subsurface lesions and/or mineralize exposed dentin tubules in a tooth, the anionic and cationic components are mixed with water and/or saliva to form a mixed aqueous composition having a pH of from greater than about 4.0 to about 10.0, which is then applied to the tooth. Because of the partial water-solubility of the calcium salt, the calcium cations and the phosphate anions in the mixed aqueous composition remain soluble for a period of time sufficient to allow the cations and anions to diffuse through the surface of the tooth to the subsurface and/or dentin, where the diffused cations and anions react to form an insoluble precipitate on the lesion for remineralization thereof and/or on the exposed tubule for mineralization thereof. The products may be in the form of chewing gums, lozenges, candies, edible food products, and the like.

17 Claims, No Drawings

U.S. PATENT DOCUMENTS

| | | |
|---|---|---|
| 4,824,681 A | 4/1989 | Schobel et al. |
| 4,828,823 A | 5/1989 | Li .................................. 424/52 |
| 4,828,845 A * | 5/1989 | Zamudio-Tena et al. ........ 426/5 |
| 4,837,007 A | 6/1989 | Duckworth et al. ........... 424/52 |
| 4,867,989 A * | 9/1989 | Silva et al. ...................... 426/5 |
| 4,931,272 A | 6/1990 | Dany et al. .................... 424/49 |
| 4,980,154 A | 12/1990 | Gordon ........................ 424/53 |
| 4,983,379 A | 1/1991 | Schaeffer ...................... 424/52 |
| 5,015,628 A | 5/1991 | Reynolds |
| 5,037,639 A | 8/1991 | Tung |
| 5,041,280 A | 8/1991 | Smigel ......................... 424/52 |
| 5,045,305 A | 9/1991 | Clarkson et al. ............... 424/52 |
| 5,047,031 A | 9/1991 | Constantz .................... 606/77 |
| 5,080,910 A | 1/1992 | Cherukuri et al. |
| 5,087,460 A | 2/1992 | Cherukuri et al. |
| 5,124,160 A | 6/1992 | Zibell et al. .................... 426/3 |
| 5,129,905 A | 7/1992 | Constantz .................... 606/76 |
| 5,139,769 A | 8/1992 | Gaffar et al. |
| 5,145,668 A | 9/1992 | Chow et al. ................... 424/52 |
| 5,268,167 A | 12/1993 | Tung |
| 5,378,131 A | 1/1995 | Greenberg |
| 5,427,768 A | 6/1995 | Tung ........................... 424/52 |
| 5,437,857 A | 8/1995 | Tung ........................... 424/52 |
| 5,441,749 A * | 8/1995 | Meyers et al. .................. 426/3 |
| 5,460,803 A | 10/1995 | Tung ........................... 424/57 |
| 5,522,893 A | 6/1996 | Chow et al. |
| 5,614,175 A | 3/1997 | Winston et al. |
| 5,645,853 A * | 7/1997 | Winston et al. ................ 424/48 |
| 5,711,937 A | 1/1998 | Nishida et al. |
| 5,833,954 A * | 11/1998 | Chow et al. ................... 424/47 |
| 5,858,333 A * | 1/1999 | Winston et al. ................ 424/48 |
| 5,958,380 A * | 9/1999 | Winston et al. ................ 424/48 |
| 6,159,448 A * | 12/2000 | Winston et al. ................ 424/52 |

\* cited by examiner

PRODUCTS AND METHODS FOR THE REMINERALIZATION AND PREVENTION OF DEMINERALIZATION OF TEETH

This application is a continuation application of U.S. Ser. No. 08/722,458, filed Sep. 27, 1996, now abandoned.

BACKGROUND OF THE INVENTION

This invention relates to improved products and methods for remineralizing subsurface lesions in teeth and for mineralizing exposed tubules in dentin so as to prevent demineralization thereof. More particularly, this invention relates to solid dentifrice products containing cationic and anionic salts having different solubilities in water and to methods of using such products to remineralize subsurface lesions in teeth and/or to mineralize exposed tubules in dentin.

The primary component of the enamel and dentin in teeth is calcium phosphate in the form of calcium hydroxyapatite. While highly insoluble at normal oral pHs, the calcium phosphate in the teeth tends to be relatively soluble in acidic media. Consequently, carious lesions can form in the subsurface of a tooth when such tooth is exposed to acids formed from the glycolysis of sugars caused by various oral bacteria.

Because saliva is supersaturated with respect to calcium and phosphate ions, saliva helps protect teeth against demineralization and can slowly remineralize teeth which have become demineralized by acids. It is well known that the presence of fluoride ions can enhance the natural remineralization process and this is one of the accepted mechanisms by which fluoride toothpastes, and rinses protect against caries. However, the efficacy of fluoride-containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva, the addition of higher levels of dissolved calcium and phosphate ions is not easily accomplished.

Remineralization of dental enamel has been carried out experimentally, both in vivo and in vitro. Some studies have concentrated on the remineralizing properties of saliva and of synthetic solutions supersaturated with respect to hydroxyapatite. Such studies comprise the subject matter of U.S. Pat. No. 3,679,360 (Rubin) and U.S. Pat. No. 4,097,935 (Jarcho).

Generally, the supersaturated solutions or slurries used in the aforementioned Rubin and Jarcho patents for remineralization experiments have been prepared from a single form of calcium phosphate. When a carious lesion is flooded with one of these supersaturated solutions, the calcium and phosphate ions in the form of precipitated hydroxyapatite remineralize the lesion. However, use of these solutions is impractical for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because such solutions cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solution, the pH of the solution changes. Unless the old solution is removed from contact with the tooth material, the solution may become too acidic or alkaline and may damage the dental tissue.

U.S. Pat. No. 4,080,440 (Digiulio et al) discloses a metastable solution of calcium and phosphate ions at a low pH (between 2.5 and 4.0) under which conditions the solubility of calcium phosphate salts is high. After penetration of the solution into demineralized enamel, remineralization results from the precipitation of calcium phosphate salts when the pH rises. Fluoride ions can be included in the metastable solution. A significant disadvantage of the use of metastable solutions is that the relatively low pH might demineralize the dental enamel and/or injure other tissue.

U.S. Pat. Nos. 4,177,258, 4,183,915 and 4,348,381 (Gaffar et al) disclose a remineralizing solution containing supersaturated concentrations of calcium ions, phosphate ions and a fluoride source stabilized by the presence of an antinucleating agent such as diamine tetramethylenephosphonic acid, ethylenediamine tetramethylenephosphonic acid and 2-phosphonobutane-tricarboxylic acid-1,2,4, or the water-soluble salts thereof. This solution is preferably adjusted to the neutral pH range where the solution is alleged to most effectively remineralize sub-surface lesions. Even though the antinucleating agent would be expected to stabilize the solution, equilibrium of the supersaturated concentrations is still found difficult to maintain and avoid precipitation of hydroxyapatite and changes in the pH of the solution. Most importantly, in order to obtain long-term (e.g., long-term) storage stability of these solutions, the concentration of calcium phosphate and, if used, fluoride is severely limited, thus limiting the remineralization potential of the formulation.

U.S. Pat. No. 4,083,955 (Grabenstetter et al) and U.S. Pat. No. 4,397,837 (Raaf et al) disclose a process for remineralizing demineralized enamel by the consecutive treatment of tooth surfaces with separate solutions containing calcium ions and phosphate ions. In this process, fluoride ions may be present in the phosphate solutions. It is immaterial which ionic solution is used to treat the teeth first. By sequentially applying calcium and phosphate ions to the tooth surface, high concentrations of the ions are able to penetrate into lesions in solution form, where the ions precipitate as a calcium phosphate salt when ions from the second treatment solution diffuse in. While apparently successful, this method involves the inconvenience of a plurality of sequential applications, which can also be time consuming.

U.S. Pat. No. 4,606,912 (Rudy et al.) teaches a method of making a clear aqueous mouthwash solution capable of remineralizing lesions in teeth by forming an aqueous solution containing a source of calcium ions and a chelating agent for calcium ions, causing the chelation of at least 50% of the calcium ions and subsequently adding a source of phosphate ions to the aqueous solution. Here too, while somewhat effective, the addition and necessary control of the amount of chelating agent makes the concept impractical.

Another problem with known remineralization techniques is that the remineralization may stop before the lesion is completely remineralized due to build-up of the remineralized tooth material in or on the outer layer of the tooth's surface. This build-up occurs when the rate of remineralization is too fast and prevents the diffusion of the mineral into the deeper regions of the lesion, thus thwarting the full remineralization of the tooth.

U.S. Pat. Nos. 5,037,639; 5,268,167; 5,437,857; 5,427,768; and 5,460,803 (all to Tung) involve the use of amorphous calcium compounds such as amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite).

Remineralization is accomplished by bringing the amorphous compound into contact with the dental tissue. This can be done directly, i.e., putting an amorphous compound directly on.the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable.

The aforementioned patents to Tung also teach the use of two-part solutions wherein a first part contains phosphate salt(s) and a second part contains calcium salt(s), wherein either the first part or the second part further contains carbonate salt(s). In addition, the Tung patents teach solutions formed by dissolving in water a solid powder containing calcium salt(s), phosphate salt(s), and carbonate salt(s). These solutions are then applied to dental tissue. The Tung patents further teach the use of non-carbonated solid powders containing mixtures of calcium salts and phosphate salts which can be applied directly to the tooth or dispersed in gel, chewing gum, or other non-aqueous mediums such as toothpaste which is placed in contact with the tooth. The patents teach that these powders are easily dissolved in saliva and then reprecipitated as an amorphous calcium phosphate compound. However, the Tung patents do not disclose the pHs of aqueous solutions formed from the non-carbonated solid powder.

Effective remineralizing/mineralizing products and methods are continually desired which do not require the presence of carbonate salts to achieve stability, remineralization and/or mineralization. It is also continually desirable to provide remineralizing/mineralizing products and methods which directly form hydroxyapatite at the subsurface of the tooth rather than first forming an amorphous calcium phosphate as an intermediate. In addition, it is continually desirable to provide a remineralization product in the form of a one-part, stable remineralizing composition which is not negatively affected by a rise in pH or temperatures or which can efficiently remineralize teeth. Finally, there is a continual need for a method of remineralizing dental enamel which employs a stable, one-part remineralizing product which does not require excessive amounts of calcium and phosphate salts or inordinately long, frequent or sequential exposure times.

Remineralizing/mineralizing one-part and two-part products which overcome many of the aforementioned problems are disclosed in copending, commonly assigned U.S. patent application Ser. No. 08/512,473 (filed Aug. 8, 1995); Ser. No. 08/465,875 (filed Jun. 6, 1995); Ser. No. 08/512,286 (filed Aug. 8, 1995); and Ser. No. 08/512,287 (filed Aug. 8, 1995).

Application Ser. No. 08/512,473 discloses one-part and two-part products and methods of using same to remineralize subsurface lesions. The one-part and two-part products contain at least one water-soluble calcium salt, at least one water-soluble divalent metal salt wherein the divalent metal is other than calcium and at least one water-soluble phosphate salt. In the two-part products, the calcium and divalent metal salts are disposed in a first discrete component, and the phosphate salt(s) is disposed in a second discrete component. The two-part product may further contain a dispensing means for allowing the first and second components to be simultaneously dispensed from the product so as to permit the dispensed first and second components to simultaneously contact the tooth or teeth being treated. The aqueous solution formed by mixing the salts used in the one-part and two-part products has a pH of from about 4.0 to about 7.0.

Application Ser. No. 08/465,875 discloses a two-part product and method of using same for remineralizing dental enamel, wherein the product contains a first discrete component containing at least one water-soluble calcium salt and a second discrete component containing at least one water-soluble phosphate salt and at least one water-soluble fluoride salt. The product may further contain a means for allowing the first and second components to be simultaneously dispensed from the product. The first and second components of the product each have a pH such that when the two components are mixed to form an aqueous mixed solution, the solution has a the pH of from about 4.5 and 10.0.

Application Ser. No. 08/512,286 is directed to a chewing gum product and method of using same for remineralizing subsurface lesions in teeth, wherein the product contains a water-soluble cationic portion composed of at least one water-soluble calcium salt and at least one water-soluble, non-toxic divalent metal salt-wherein the divalent metal is other than calcium; a water-soluble anionic portion containing at least one water-soluble phosphate salt; and a gum base. The anionic and cationic portions are disposed in the product such that chewing of the product in the presence of water and/or saliva causes the anionic and cationic portions to be simultaneously released into the water and/or saliva so as to form a mixed aqueous solution therewith. The anionic and cationic portions each have a pH when dissolved in water and/or saliva such that the mixed aqueous solution has a pH of from about 4.0 to 7.0.

Application Ser. No. 08/512,287 is directed to one-part, non-aqueous products and methods of using same for remineralizing subsurface lesions, wherein the products contain at least one water-soluble calcium salt; at least one water-soluble phosphate salt; either a stabilizer or a hydrophilic, non-aqueous, water-soluble vehicle; and, optionally, at least one water-soluble fluoride salt. When the components are mixed with water or saliva to form an aqueous mixed solution, the solution has a pH of from about 4.5 to about 10.0.

In the one-part and two-part products disclosed in the foregoing applications, the cationic and anionic components are kept separate from one another until use of the product. In addition, the cations and anions are delivered simultaneously to the surface of the tooth being treated. These factors, along with the pH of the aqueous solution and the use in some cases of at least one water-soluble divalent metal salt, are helpful to allowing the cations and anions to have ample time to diffuse through the surface of the tooth to the subsurface before undergoing precipitation.

For mineralization or remineralization of enamel or dentin to occur, the concentration of calcium and phosphate ions in saliva must be above the concentration required to saturate the solution with respect to the formation of calcium hydroxyapatite, octacalcium phosphate, dicalcium phosphate dihydrate, or other form of insoluble calcium phosphate. At pHs above about 6.5, these requirements are met by the levels of calcium and phosphate in normal human saliva. However, because the concentration of calcium and phosphate ions in normal human saliva is only modest, even at pHs above 6.5, the rate of mineralization produced by normal saliva is very slow even when fluoride is present to catalyze the process. When the pH is above about 7, raising the concentration of calcium and phosphate ions much beyond that normally present in saliva does not, however, significantly increase remineralization. Because of the high insolubility of calcium phosphate salts above pHs of about 7, excessively rapid precipitation occurs which does not allow time for the ions to penetrate the tooth.

At pHs below about 7, significant remineralization will occur only if the concentration of calcium and phosphate ions in the saliva is above the concentration required to saturate the solution with respect to the formation of dicalcium phosphate dihydrate. Under these pH conditions, it has been demonstrated that remineralization can be accelerated by increasing the degree of supersaturation in saliva. Inasmuch as the solubility of dicalcium phosphate increases with decreasing pH, it has been found that when lesions are remineralized with solutions having a pH in the range of 4.5 to 7.0 and containing supersaturated quantities of calcium and phosphate ions, the optimum concentration of calcium ions needed to maximize the process increases with decreasing pH. Below a pH of about 4.0, dicalcium phosphate dihydrate becomes the stable precipitating species from supersaturated solutions. Under these pH conditions, it takes very high levels of calcium and phosphate to saturate the solutions. Under such conditions, there is a real danger with fairly high concentrations of calcium and phosphate that the solution will be undersaturated and demineralization of the teeth being treated will occur.

It has also been found that the simultaneous provision of very high calcium and phosphate ion concentrations can result in premature precipitation of the calcium salt before the ions can penetrate the tooth or premature precipitation so as to block the entrances of the pores in tooth enamel and dentin and thereby prevent further remineralization.

Thus, a problem apparently exists in that to control untimely precipitation, the concentration of either the dissolved calcium ions or the dissolved phosphate ions needs to be limited. This in turn would be expected to disadvantageously limit the maximum rate of mineralization or remineralization which could be accomplished.

In addition, the use of very high calcium and fluoride ion concentrations can result in premature precipitation of the fluoride ions before these ions can penetrate the tooth. As mentioned previously herein, fluoride ions can enhance the natural remineralization process. However, sufficient levels of fluoride ions are generally required to be present. Calcium cations and fluoride anions precipitate to form calcium fluoride, a salt which is sparingly soluble in water. The formation of calcium fluoride is undesirable since it reduces the amount of free fluoride anions available for use in the remineralization process. Thus, it is desirable to provide a remineralizing product wherein the solution used to treat the teeth contains sufficient levels of dissolved fluoride anions to enhance the remineralization of the subsurface lesions.

Although the remineralization products disclosed in the aforementioned copending, commonly assigned patent applications are stable, it is continually desirable to provide alternative products which minimize the risk of premature precipitation of the cations and anions, particularly of the fluoride anions.

Accordingly, a primary object of this invention is to provide products and methods for the remineralization and the prevention of demineralization of human teeth, wherein the products and methods are capable of effectively incorporating calcium ions, phosphate ions and, if present, fluoride ions into the subsurface of a tooth.

A further object of this invention is to provide products and methods for the remineralization and the prevention of demineralization of human teeth, wherein the precipitation of the calcium, phosphate and, if present, fluoride ions is substantially avoided prior to diffusion of the ions into the subsurface of the tooth without reducing the rate of remineralization at the subsurface of the tooth.

Another object of this invention is to provide products and methods for the remineralization and the prevention of demineralization of human teeth, which do not require excessive amounts of solution or inordinately long or frequent exposure times.

Still another object of the present invention is to provide products for the remineralization and the prevention of demineralization of human teeth, wherein the products are easily usable by the consumer and do not differ significantly, in flavor or appearance, from customary dental cosmetics.

Yet another object of this invention is to provide an improved product and a method of preparing such product, wherein the product is maintainable in a single container, substrate or matrix and is capable of remineralizing lesions in the teeth and mineralizing normal teeth to prevent cariogenic lesions from forming therein.

A further object of this invention is to provide remineralizing/mineralizing products and methods which can directly form hydroxyapatite in the subsurface of a tooth subsurface without first forming an amorphous calcium phosphate as an intermediate.

Yet another object of the present invention is to provide products having the characteristics set forth in the foregoing objects and which are in the form of a chewing gum, a lozenge, candy, food product, tablet, powder, dragee, bon bon and the like.

A further object of the present invention is to provide remineralization/mineralization methods using products having the characteristics set forth in the preceding objects.

These and other objects which are achieved according to the present invention can be readily discerned from the following description.

SUMMARY OF THE INVENTION

The present invention provides effective remineralizing/mineralizing solid products and methods of using same which overcome the aforementioned problems and achieve the foregoing objects.

Specifically, the present invention provides solid products for remineralizing subsurface lesions and/or mineralizing exposed dentin tubules in teeth, containing:

(a) a cationic component containing at least one partially water-soluble calcium salt;

(b) an anionic component containing at least one water-soluble phosphate salt; and (c) a separating component for separating components (a) and (b) in the product; the product being capable of releasing, preferably simultaneously, components (a) and (b) into water and/or saliva when the product is mixed with the water and/or saliva;

wherein components (a) and (b) have a pH in water such that a mixed aqueous composition formed by mixing components (a) and (b) with water and/or saliva has a pH of from about 4.0 to about 10.0;

further wherein the cationic component contains an amount of the calcium salt such that in the mixed aqueous composition a first portion of the calcium salt exists as dissolved calcium cations and a second portion of the calcium salt exists as undissolved calcium salt, the anionic component comprising an amount of the phosphate salt such that the mixed aqueous composition further contains dissolved phosphate anions released by the phosphate salt.

Remineralization and/or mineralization is effected by mixing (e.g., by chewing, sucking or eating) the above-described solid product with water and/or saliva such that the solid product releases components (a) and (b) in the water and/or saliva to form the mixed aqueous composition, and then applying the mixed aqueous composition to at least one surface of at least one tooth for a period of time sufficient to allow the dissolved calcium cations and the dissolved phosphate anions to diffuse through the surface of the tooth to the subsurface and/or dentin portion, wherein the diffused cations and anions precipitate to form an insoluble compound on the subsurface lesion and/or on the exposed dentin tubule, thereby remineralizing such lesion and/or mineralizing such exposed tubule.

In the present invention, when the mixed aqueous composition is applied to the tooth (or teeth), the dissolved calcium cations and the dissolved phosphate anions in the aqueous composition do not immediately precipitate but rather diffuse through the surface of the tooth to the subsurface and/or dentin thereof, where the ions then precipitate to form an insoluble compound on the demineralized subsurface lesion(s) and/or on the exposed dentin tubule(s).

This invention is based on the discovery that such delayed precipitation of the calcium cations and the phosphate anions until such ions have diffused through the tooth surface to the subsurface and/or dentin can be achieved by using in the cationic component at least one calcium salt having partial water-solubility at a pH of from about 4.0 to about 10.0. With the use of the partially water-soluble calcium salt(s) in the cationic component of the products of this invention, the calcium cations and the phosphate anions in the mixed aqueous composition used to treat the tooth are able to remain soluble for the period of time sufficient to allow the cations and anions to diffuse through the surface of the tooth to the subsurface and/or dentin thereof, where, as stated above, the ions react to form an insoluble precipitate on the demineralized lesion(s) and/or exposed tubule(s).

An important advantage of using the partially water-soluble calcium salt(s) in the present invention is that at any point in time the low concentration of calcium cations does not insolubilize the phosphate anions which are needed for remineralization and/or mineralization. The undissolved calcium salt in the mixed aqueous composition will release additional calcium cations as dissolved calcium cations in the mixed aqueous composition are used up or swallowed during the remineralization and/or mineralization process. The dissolved calcium cations and the dissolved phosphate anions are able to remain soluble for a period of time sufficient to permit the cations and anions to diffuse through the tooth surface to the subsurface and/or dentin of the tooth before forming a precipitate. Instead of precipitating on the surface of the tooth, the calcium cations and the phosphate anions released by the products of this invention will form an insoluble precipitate on the demineralized lesion(s) in the tooth subsurface and/or on the exposed tubule(s) in the dentin portion of the tooth.

Another advantage resulting from the use of the partially water-soluble calcium salt(s) in the present invention is that high concentrations of the undissolved calcium salt can be added to the dentifrice formulation without the danger of excessive concentrations of calcium cations being released at any one time to the saliva.

A further advantage resulting from the use of the partially water-soluble calcium salt(s) in the present invention is that, as the calcium cations in the mixed aqueous composition are used up (i.e., precipitated), the undissolved calcium salt can release additional calcium cations to the composition so as to maintain the rate of the remineralization and/or mineralization process.

Thus, the use of the partially water-soluble calcium salt(s) in the present invention provides a practical way to ensure close to optimum levels of calcium cations throughout the remineralization and/or mineralization process.

The products of the present invention provide substantially improved remineralization and mineralization as compared with the prior art products discussed hereinabove.

In addition, the methods of the present invention overcome the disadvantages of the prior art methods discussed hereinabove in that the methods of this invention effect subsurface remineralization rather than surface remineralization. Since dental caries begins as a subsurface demineralization of the dental enamel, subsurface remineralization arrests and repairs the carious lesion before any permanent structural damage to the tooth occurs.

Furthermore, the methods of the present invention do not require preparation of the enamel surface, capping of the tooth, or removal of decay products.

In addition, consumers may conveniently practice the methods of the present invention without substantially changing their dental care habits.

DETAILED DESCRIPTION OF THE INVENTION

The present invention is directed to solid products and methods of using same to remineralize subsurface lesions in teeth and/or to mineralize exposed tubules in dentin.

As used herein, the term "solid product" refers to a product having a hard consistency or a gum-like consistency and which can be eaten, sucked or chewed in the oral cavity. Non-limiting examples of solid products within the scope of this invention include chewing gums, lozenges, candy products, edible food products, tablets, dragees, bon bons and the like.

The products of this invention contain (a) a cationic component containing at least one partially water-soluble calcium salt, (b) an anionic component containing at least one water-soluble phosphate salt and (c) a separating component for separating the cationic and anionic components in the product. In preferred embodiments, the cationic component of the products of this invention further contains at least one water-soluble salt of a divalent metal other than calcium. In addition, the anionic component of the products of this invention may further contain at least one water-soluble fluoride salt.

As used herein, the term "partially water-soluble" with respect to the calcium salt component refers to any toxicologically harmless calcium salt having a solubility in water which is greater than that of dicalcium phosphate dihydrate in an aqueous solution having a pH of about 7.0 and a temperature of about 25° C. but which is less than that solubility which would release more than about 1400 ppm of calcium cations in such aqueous solution. In an aqueous solution having a pH of about 7.0 at a temperature of about 25° C., dicalcium phosphate dihydrate generally releases about 40 ppm of calcium cations. Thus, the calcium salt(s) used in the present invention generally has a solubility in water such that the salt releases more than about 40 ppm but no more than about 1400 ppm of calcium cations in an aqueous solution having a pH of about 7.0 at a temperature of about 25° C. Preferably, the calcium salt(s) used in this invention has a solubility in water such that the salt(s) releases from about 100 ppm to no more than about 1400 ppm of calcium cations in such aqueous solution.

The term "water-soluble" as used herein with respect to the phosphate, fluoride and divalent metal salts suitable for use in the present invention refers to a solubility such that the salts are each capable of releasing more than 1400 ppm of ions into an aqueous solution having a temperature of about 25° C. and a pH of about 7.0.

As stated hereinabove, the cationic component of the products of this invention contains an amount of the partially water-soluble calcium salt such that the aqueous mixed composition formed by mixing the cationic and anionic components with water and/or saliva contains a first portion of the calcium salt as dissolved calcium cations and a second portion of the calcium salt as undissolved calcium salt. Preferably, the aqueous mixed composition will contain from about 100 ppm to no more than about 1400 ppm of the dissolved calcium cations and at least about 500 ppm of the undissolved calcium salt. More preferably, the mixed aqueous composition will contain from about 100 ppm to no more than about 800 ppm of the dissolved calcium cations and at least about 2000 ppm of the undissolved calcium salt. Most preferably, the mixed aqueous composition will contain from about 100 ppm to about 500 ppm of the dissolved calcium cations and from about 2000 ppm to about 3000 ppm of the undissolved calcium salt.

The anionic component of the products of this invention contain at least one water-soluble phosphate salt in an amount such that the mixed aqueous composition will contain dissolved phosphate anions. The mixed aqueous composition will preferably contain at least about 100 ppm, more preferably from about 500 ppm to about 40,000 ppm, of the dissolved phosphate anions. A portion of the phosphate salt may be present in the mixed aqueous composition as undissolved phosphate salt.

As stated previously herein, the cationic component of the products of this invention preferably further contain at least one non-toxic, water-soluble salt of a divalent metal other than calcium. The cationic component contains an amount of the divalent metal salt such that the mixed aqueous composition contains dissolved divalent metal cations. The presence of such dissolved divalent metal cations in the mixed aqueous composition helps to stabilize the composition against premature precipitation of the calcium cations and the phosphate anions so as to help in allowing the remineralizing cations and anions to diffuse through the tooth surface to the subsurface lesion(s) and/or exposed dentin tubule(s) prior to precipitating. As a result, when an effective amount of dissolved divalent metal cations is present in the mixed aqueous composition, the subsurface lesion is more effectively remineralized and/or the exposed dentin-tubule(s) is more effectively mineralized.

The mixed aqueous composition will preferably contain at least about 100 ppm, more preferably from about 500 ppm to about 40,000 ppm, of the dissolved divalent metal cations.

The anionic component of the products of this invention may further contain at least one water-soluble fluoride salt, the caries-prophylactic activity of which has long been established. However, because of the potential for fluorosis or other toxic effects, high levels of such fluoride salt(s) in the products of this invention are undesirable. Preferably, the concentration of fluoride anions in the mixed aqueous composition applied to the teeth should not exceed about 1000 ppm. However, low concentration levels of the fluoride anions can be useful in the mixed aqueous compositions used in the present invention. Such low concentration levels of fluoride anions preferably range from about 1 ppm to about 100 ppm, most preferably from about 1 ppm to about 10 ppm.

The cationic component of the solid products of this invention preferably contain from about 0.05% to about 15.0%, more preferably from about 0.10% to about 10.0%, by weight of the partially water-soluble calcium salt. In preferred embodiments, the cationic component further contains at least 0.001%, more preferably from about 0.0001% to about 2.0%, and most preferably from about 0.01% to about 1.0%, by weight of the divalent metal salt(s) previously discussed herein. The anionic component of the products of this invention preferably contains from about 0.05% to about 15.0%, more preferably from about 0.10% to about 10.0%, by weight of the water-soluble phosphate salt(s). The anionic component may further contain no more than about 0.10% by weight, more preferably from about 0.0001% to about 0.01%, most preferably from about 0.0001% to about 0.001%, by weight of the at least one water-soluble fluoride salt.

The products of this invention generally contain a molar ratio of the calcium salt(s) to the phosphate salt(s) of preferably from about 0.01:1 to about 100:1. Most preferably, the concentration of the calcium salt(s) and the concentration of the phosphate salt(s) are essentially the same in the products of this invention. The concentration of the calcium salt(s) always exceeds the solubility of such salt, whereas the concentration of the phosphate salt(s) may be as high or even higher than the solubility thereof.

Non-limiting examples of calcium salts of partial water-solubility suitable for use in this invention include calcium sulfate, anhydrous calcium sulfate, calcium sulfate hemihydrate, calcium sulfate dihydrate, calcium malate, calcium tartrate, calcium malonate, calcium succinate, and mixtures of the foregoing. Calcium sulfate is preferred.

The partially water-soluble calcium salt component of the products of this invention can be prepared in situ, for example, by preparing mixtures of an acid such as, e.g., tartaric acid, and a water-soluble calcium salt such as, e.g., calcium nitrate, and adjusting the pH as needed.

In the present invention, the principle known as the "common ion effect" can be used to control the solubility of the partially water-soluble calcium salt used in the present invention and to optimize calcium release and fluoride stability. To achieve the common ion effect, a water-soluble "common anion" salt can be added to the cationic component of the products of this invention wherein the anion of the salt is the same as the anion present in the calcium salt used in the cationic component. In the present invention, the preferred "common anion" salts are the sodium, potassium and ammonium salts. However, an anion which is part of another functional ingredient may also be added. For example, the use of magnesium sulfate in a calcium sulfate-based formulation would supply at least some of the needed sulfate anion.

Suitable water-soluble inorganic phosphate salts for use in the present invention include, for example, alkali salts and ammonium salts of orthophosphoric acid, such as, e.g., potassium, sodium or ammonium orthophosphate; monopotassium phosphate; dipotassium phosphate; tripotassium phosphate; monosodium phosphate; disodium phosphate and trisodium phosphate.

Suitable fluoride salts for use in the present invention include the alkali fluorides such as sodium, potassium, lithium or ammonium fluoride, tin fluoride; indium fluoride; zirconium fluoride; copper fluoride; nickel fluoride; palladium fluoride; fluorozirconates such as sodium, potassium or ammonium fluorozirconate or tin fluorozirconate; fluorosilicates; fluoroborates; and fluorostannites.

Organic fluorides, such as the known amine fluorides, are also suitable for use in the products of the present invention.

Water-soluble alkali metal monofluorophosphates such as sodium monofluorophosphate, lithium monofluorophosphate and potassium monofluorophosphate, (the sodium monofluorophosphate being preferred) may be employed. In addition, other water-soluble monofluorophosphate salts may be employed, including, for example, ammonium monofluorophosphate, aluminum monofluorophosphate, and the like. If monofluorophosphate salts are used as the fluoride source in two-phase systems, these salts could be present in the first phase along with the calcium cations without departing from the present invention. However, this is less desirable due to the potential loss of fluoride as a result of the formation of sparingly soluble calcium fluoride.

The divalent metal salt(s) which can be used in the products of the present invention may be any water-soluble, non-toxic divalent metal compound which will stabilize the calcium, phosphate and fluoride ions so that these ions do not rapidly or prematurely precipitate before diffusing into the teeth. In practice, however, it has been found that at least one member selected from the group consisting of magnesium, strontium, tin, and zinc, with magnesium being preferred, is the most effective divalent metal in stabilizing the system.

Suitable magnesium compounds include, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds include, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds include, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds include, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

In the products of this invention, either the cationic component or the anionic component so long as the product itself is solid as defined previously herein.

If the cationic component is aqueous, the aqueous cationic component may contain an amount of dissolved calcium cations released by the calcium salt and an amount of an undissolved form of the calcium salt. The aqueous cationic component preferably contains no more than about 0.14% by weight, more preferably no more than about 0.08%, most preferably from about 0.01% to about 0.05%, by weight of the dissolved calcium cations. In addition, the aqueous cationic component preferably contains at least about 0.05%, more preferably at least about 0.20%, most preferably from about 0.20% to about 0.30%, by weight of the undissolved form of the calcium salt.

If the cationic component further contains at least one salt of a divalent metal other than calcium, as discussed previously herein, the aqueous cationic component may further contain dissolved divalent metal cations released by the divalent metal salt.

If the cationic component also contains a "common-anion" salt as previously described herein, the aqueous cationic component may further contain dissolved ions released by the common-anion salt.

If the anionic component is aqueous, the aqueous anionic component may contain dissolved phosphate anions released by the phosphate salt. If the anionic component further contains at least one water-soluble fluoride salt as previously discussed herein, the aqueous anionic component may further contain dissolved fluoride anions released by the fluoride salt.

The products of this invention may be in the form of one-part products or two-part products.

The one-part products of this invention contain the anionic and catiohic components disposed in a solid, non-aqueous solid carrier medium which serves as the separating component (c). The carrier medium may be water-soluble (i.e., hydrophilic) or water-insoluble (i.e., hydrophobic), and is capable of releasing the components (a) and (b) into water and/or saliva upon contact of the carrier medium with the water and/or saliva. Preferably, the carrier medium is capable of simultaneously releasing the components (a) and (b) into the water and/or saliva.

As will be discussed in greater detail later herein, one preferred embodiment of the one-part product of this invention is a chewing gum product wherein the carrier medium is a hydrophobic gum base.

Two-part products of this invention generally contain:
(A) a first discrete part containing the cationic component;
(B) a second discrete part containing the anionic component;
(C) a physical barrier separating the first and discrete parts, the physical barrier serving as the separating component, wherein upon contact of the first and second parts with water and/or saliva such first and second discrete parts are capable of releasing, preferably simultaneously releasing, the cationic and anionic components, respectively, into the water and/or saliva.

In one embodiment, the two-part product is a two-layer structure composed of a first discrete layer and a second discrete layer, wherein the first discrete layer contains the first discrete part and the second discrete layer contains the second discrete part. Upon mixing of the product with the water and/or saliva the first and second discrete layers are capable of releasing the first and second discrete parts, respectively, into the water and/or saliva to form the mixed aqueous composition.

The two-part product may also be a multi-layer product wherein wherein alternating layers contain a different discrete part, e.g., a first layer will contain the first discrete part; a second, adjacent layer will contain the second discrete part; a third, adjacent layer will contain the first discrete part; and so on.

In another embodiment, the two-part product of this invention has a "sheath-core" configuration, wherein such product contains a water-soluble core and a water-soluble sheath coating encapsulating the core. One discrete part is disposed in the core and the other discrete part is disposed in the sheath encapsulating coating surrounding the core portion. The discrete part disposed in the core may be liquid or solid and may be aqueous or non-aqueous. The sheath encapsulating coating is composed of a hydrophilic solid material. Upon mixing of the product with the water and/or saliva, the sheath encapsulating coating and the core are capable of releasing the cationic and anionic components in-to the water and/or saliva to form the mixed aqueous composition.

The core of such a sheath-core type product may be liquid or solid, aqueous or non-aqueous. The sheath encapsulating coating is solid.

Hydrophilic (water-soluble) solid carrier mediums which may be used in the products of this invention include any of such carrier mediums which are conventionally used in such solid products as lozenges, candies, edible food products, and the like. Preferred hydrophilic solid carrier mediums are composed of hydrophilic organic polymers. Suitable hydrophilic polymers include, e.g., gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, and the like. Polyvinyl acetate is an example of a water-insoluble polymer which can be included as an additional coating component to moderate the hydrophilicity of a hydrophilic polymer coating.

Water-insoluble (hydrophobic) solid carrier mediums which can be used in this invention include, e.g., water-insoluble polymers such as, for example, polyvinyl acetate, polyacrylamide, polyvinyl chloride, polystyrene, polyethylene, polyurethane, and the like.

As mentioned previously herein, another embodiment of the product of this invention is a water-soluble, dry-mix product capable of being combined with a non-aqueous solid carrier medium or with an aqueous liquid medium to form a remineralizing/mineralizing product. Such dry-mix product contains (a) from about 1.0% to about 80.0% by weight of the partially water-soluble calcium salt(s) and (b) from about 1.0% to about 80.0% by weight of the water-soluble phosphate salt(s). In preferred embodiments, the dry mix product of this invention further contains from about 0.1% to about 20.0% by weight of the divalent metal salt(s) discussed previously herein. In addition, the dry mix product may also contain up to about 0.01% by weight of the fluoride salt(s) discussed hereinabove.

The dry-mix product may be mixed with a solid carrier medium such as, e.g., a gum base which is later contacted with water and/or saliva to form the mixed aqueous composition which is then applied to the teeth. Alternatively, the dry-mix product may be directly diluted with water and/or saliva to form the mixed aqueous composition.

The solid product of this invention preferably contains from about 70% to about 99.9%, more preferably from about 80% to about 99.8%, by weight of the solid carrier medium.

In the present invention, the mixed aqueous composition is formed by mixing the solid product of this invention with water and/or saliva, preferably in the oral cavity. Preferably, the mixing of the product with the water and/or saliva is achieved by chewing (in the case of chewing gum products), sucking (in the form of, e.g., lozenges, candy, and the like) or eating (in the case of, e.g., edible food products). With the one-part products of this invention, the mixed aqueous composition is formed by mixing the product with water and/or saliva such that the carrier medium releases (preferably simultaneously) the cationic and anionic components therefrom into the oral cavity. With the two-part products of this invention, the mixed aqueous composition can be formed by mixing the product with water and/or saliva such that one discrete part releases the cationic component into the water and/or saliva and the other discrete part releases the anionic component into the water and/or saliva, the anionic and cationic components preferably being released simultaneously into the water and/or saliva.

In the methods of this invention, the tooth (or teeth) are treated with the mixed aqueous composition formed from the products of this invention as described above. The tooth is treated with the mixed aqueous composition for a period of time sufficient to allow diffusion of the ions to the subsurface and/or dentin where the ions then precipitate an insoluble compound onto the subsurface lesion(s) and/or onto the exposed dentin tubule(s). In this way, the subsurface lesion(s) is remineralized and/or the exposed dentin tubule(s) is mineralized.

The mixed aqueous composition used to treat the teeth in accordance with this invention has a pH of from about 4.0 to about 10.0, preferably from greater than about 4.0 to about 7.0, more preferably from about 4.5 to about 6.5, and most preferably from about 5.00 to about 5.75. At a pH within such ranges, enough of the calcium cations, phosphate anions and, if present, fluoride anions, in the mixed aqueous composition remain soluble for a period of time sufficient to allow the ions to diffuse through the surface of the tooth to the subsurface and/or dentin thereof, where the diffused ions then precipitate to form an insoluble compound on the subsurface lesion(s) and/or exposed dentin tubule(s), thereby remineralizing the subsurface lesion(s) and/or mineralizing the exposed dentin tubule(s), respectively.

If the mixed aqueous composition has a pH below about 3, demineralization will occur rapidly. A pH below about 2.5 is undesirable from a safety standpoint. Thus, the anionic and cationic components of the products of this invention have a pH in water such that the mixed aqueous composition formed therefrom has a pH within the aforementioned ranges.

The products of this invention may contain suitable pH-adjusting compounds, i.e., acids, bases or buffers, to ensure that the mixed aqueous compositions formed therefrom will have a pH within the ranges mentioned above. The pH of the mixed aqueous composition may be controlled by adding to the product or the mixed aqueous composition any acid, base or buffer which is safe for use in the oral cavity and which yields the desired pH at the amount used. Examples of suitable acids include acetic acid, phosphoric acid, citric acid, and malic acid. Suitable buffers which can be used include, e.g., sodium citrate, tartrate, lactate, benzoate, carbonate, bicarbonate, malate, disodium hydrogen phosphate, sodium dihydrogen phosphate and the like. The particular salts used in the anionic and cationic components of the products of the present invention can be selected to obtain the desired pH. For example, a combination of monobasic, dibasic and/or tribasic alkali metal or ammonium phosphate salt may be selected to provide the target pH.

The pH of the mixed aqueous composition remains relatively constant after its formation in or introduction into the oral cavity. Under some conditions, calcium fluoride phosphate may precipitate at the pH of the mixed aqueous composition in the oral cavity, but most surprisingly, while some precipitation may occur immediately, substantially greater amounts of calcium, phosphate and, if present, fluoride ions remain in solution to diffuse through the tooth surface into the subsurface and/or dentin, where the ions then precipitate to form an insoluble compound so as to remineralize subsurface lesions and/or mineralize exposed dentin tubules. Such delayed precipitation is due in large part to the use of the partially water-soluble calcium salt. The presence of divalent metal cations in the mixed aqueous composition also helps to delay precipitation until after diffusion of the ions has occurred. It is believed that the ability of the mixed aqueous composition to provide ions for remineralization and/or mineralization is greatest upon the formation or introduction thereof in the oral cavity, thereafter decreasing, but at a rate less than that encountered when not using the partially water-soluble calcium salt and/or the divalent metal cations.

The length of time in which the tooth is treated with the mixed aqueous composition is important to the present invention. The period of treatment needs to be long enough to allow diffusion of the ions through the tooth surface to the demineralized subsurface lesion(s) and/or exposed dentin tubule(s). Such period of treatment is preferably at least about 2 minutes, more preferably at least about 5 minutes, and most preferably at least about 15 minutes. The ability of the products of this invention to provide such an extended time period for diffusion accrues from the use in this invention of the one or more partially water-soluble calcium salts. The use of the divalent metal salt(s) in the preferred embodiments of the products of this invention further help to allow a time period long enough to permit diffusion before precipitation.

As stated previously herein, the ions which have diffused through the tooth surface form an insoluble precipitate on the demineralized subsurface lesion(s) and/or on the exposed dentin tubule(s). Although many precipitates are within the broad scope of this invention, it is preferred that the precipitate render the remineralized subsurface and/or mineralized dentin of the tooth treated in accordance with this invention more resistant to demineralization than was the original enamel. Thus, the preferred precipitate is one which is less soluble than the original enamel. Tooth enamel primarily contains a slightly carbonated apatite. If the precipitating species is not carbonated, the precipitate will be somewhat less soluble than the original enamel. Therefore, when fluoride anions are not present, it is desirable that conditions be present which favor the precipitation of unsubstituted hydroxyapatite. Thus, for example, it is desirable to avoid the addition of carbonates or bicarbonates to nonfluoride compositions. On the other hand, if fluoride salts are used in the products of this invention, the apatite will incorporate fluoride anions, thus rendering the precipitate more resistant to demineralization than was the original enamel. However, even when fluoride anions are not directly added to the remineralizing/mineralizing mixed aqueous composition used in the present invention, it has been found that the teeth treated with such composition will absorb more fluoride when subsequently treated with a fluoride-containing product (e.g., a fluoride toothpaste) than teeth which had not been pretreated with such composition.

Thus, the precipitate formed in the present invention is preferably a calcium phosphate or a hydroxyapatite.

Therefore, use of the products of this invention not only remineralizes the demineralized enamel and/or mineralize the exposed dentin tubules but also renders such remineralized enamel and/or mineralized dentin tubule more resistant to subsequent demineralization than was the original enamel or tubule.

The mixed aqueous composition formed from the products of this invention and the insoluble precipitate formed from the mixed aqueous composition must both have acceptable levels of toxicity. In other words, the particular ions, in the amounts used in the remineralization and/or mineralization process, must be non-toxic. Furthermore, such composition and precipitate should be otherwise compatible in the oral environment.

It has been found that even with the use of the divalent metal salt(s) discussed previously herein and the presence of the solid, non-aqueous, carrier medium, some reaction between calcium cations, phosphate anions and, if present, fluoride anions, may occur in the products of this invention during storage thereof (for example, in a closed container or package). Such reaction results in the formation of an insoluble precipitate such as calcium phosphate. To avoid this, preferred embodiments of the solid products of this invention further contain a stabilizing agent which helps to prevent the calcium and phosphate ions (and fluoride ions, if present) from reacting. Such a stabilizing agent may be used in place of the divalent metal salt(s) or may be used in addition to the divalent metal salt(s).

Suitable stabilizing agents for use in this invention include any orally acceptable material that can stabilize one or more of the calcium salt(s), phosphate salt(s) and/or fluoride salt(s) during storage of the product. Non-limiting examples of such stabilizing agents include desiccating agents, coating or encapsulating materials, and mixtures of the foregoing.

Non-limiting examples of suitable desiccating agents include magnesium sulfate, sodium sulfate, calcium sulfate, calcium chloride, and colloidal silica, e.g., colloidal silica particles sintered together in chain-like formations having surface areas of from about 50 to about 400 square meters per gram such as materials sold under the trademark Cab-O-Sil by Cabot Corporation. It is believed that such materials stabilize the products of this invention by, for example, absorbing any existing water either present in or contacted with the composition so as to prevent reaction of the calcium, phosphate and/or fluoride salts.

When used, the stabilizing agent is present in the products of this invention in an amount effective to inhibit reaction between the calcium, phosphate and/or fluoride salts in the product during storage thereof, while allowing release of sufficient calcium, phosphate and/or fluoride ions when the product is contacted with water and/saliva. The stabilizing agent is preferably present in an amount of up to about 7.5% by weight, more preferably from about 0.1% to about 5.0% by weight.

Another way to inhibit premature reaction of the anionic and cationic components of the solid products of this invention is to provide a coating on or encapsulation of one or more of the components. The presence of the coating or encapsulation material on one or more of the anionic and cationic components prevents reaction of these components with other substances, e.g., traces of water in or absorbed into the system. Preferably, the coating is edible or rinsable from the mouth.

As stated previously, the anionic and cationic components are preferably released simultaneously from the products of this invention into the water and/or saliva. Therefore, it is important that the encapsulant not impede the release of calcium cations or phosphate anions in such a way as to lead to an undesirable imbalance of the cations and anions. Suitable encapsulating or coating materials include oleophilic and other materials such as conventional edible gums, polymers which exhibit proportion ranging from hydrophilic to hydrophobic (water-insoluble), resins, waxes and mineral oils.

A preferred polymer for coating or encapsulating particles of one or more of the cationic and anionic components is selected from hydrophilic organic polymers and hydrophobic (water-insoluble) organic polymers and mixtures thereof.

Suitable hydrophilic polymers include water-soluble and water-dispersible organic polymers organic polymers. A mixture of polymers can be used, and from about 5.0% to about 95.0% by weight of a water-insoluble polymer can be included with the hydrophilic polymer.

Suitable hydrophilic polymers for coating the salt particles in this invention include, e.g., gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, and the like. Polyvinyl acetate is an example of a water-insoluble polymer which can be included as an additional coating component to moderate the hydrophilicity of a hydrophilic polymer coating.

Suitable water-insoluble polymers, alone or in combination with one or more other components, for coating the salt particles in the present invention include polyvinyl acetate, polyacrylamide, polyvinyl chloride, polystyrene, polyethylene, polyurethane, and the like.

The polymer coating can be applied to the the cationic and/or anionic components (i.e., to particles of the cationic and/or anionic components) used in this invention by conventional means such as pan coating, fluidized coating, centrifugal fluidized coating, and the like. The coating polymer is usually dissolved in a suitable solvent such as water, methanol, ethanol, acetone, tetrahydrofuran, ethyl acetate, dimethylformamide and the like, as appropriate for a selected polymer species. A coating polymer can also be applied in the form of an emulsion or suspension. After the coating medium is applied to the particles, the solvent medium is removed by evaporation, thereby forming a continuous film-coating which encapsulates the discrete crystallite particles.

The coating thickness on the surface of the salt component preferably ranges from about 0.1 to about 20 microns. The coating can contain one layer or multiple layers, and may constitute from about 0.5% to about 50.0% of the total dry weight of the coated particles.

To allow release of the cationic and anionic components from the core matrix of the encapsulated particles when the solid product of this invention is introduced into an aqueous environment, the surface coating of water-insoluble polymer may contain from about 5.0% to about 30.0% by weight of a particulate water-extractable organic or inorganic filler, such as, e.g., sodium monosaccharide or disaccharide, sorbitol powder, mannitol, and the like.

The rate of release of the salt-containing core matrix of the encapsulated particles under aqueous conditions can be controlled by the quantity and type of polymer coating on the particle surface.

Low molecular weight hydrophilic polymers will release the particle core matrix content at a relatively fast rate in the presence of moisture. High molecular weight polymers which are less hydrophilic will release at a relatively slow rate. Additional rate control is obtained by using mixtures of polymer components of varied hydrophilicity.

Polyethylene glycol or polyvinyl alcohol will release the particle core matrix at a relatively fast rate. Polyethylene oxide or partially hydrolyzed polyvinyl acetate will release at a relatively slow rate. Polyvinylpyrrolidone will release the:particle core matrix content at an immediate rate, when the encapsulated particles incorporated into the solid product are applied to the teeth.

Examples of suitable oleophilic coatings or encapsulating materials include paraffin; mineral oil; edible oils such as peanut oil, coconut oil, palm oil, or safflower oil; oleophilic organic esters such as isopropyl siloxane myristate or isopropyl palmitate; edible polysiloxanes; and the like. Encapsulating salts with a mixture of paraffin and waxes is also suitable.

The use of mineral oil as the oleophilic coating material is particularly advantageous because mineral oil will help in removing undesired bacteria during the course of treatment of the teeth with the mixed aqueous composition formed of the solid products of this invention.

The oleophilic coating should be thick enough that the coating will either readily dissolve, disperse, emulsify or disintegrate in water or saliva during chewing or sucking of the product to release the salts.

If a water-insoluble oleophilic coating, e.g. mineral oil, is used, the coating phase can be pre-emulsified with a nonionic, non-aqueous surfactant such as a hydrophilic ethoxylated sorbitan monooleate, e.g., the material sold under the trademark Tween. In this manner, when the product is placed in water or saliva, the oleophilic coating is emulsified more readily than without the emulsification agent being present. Other similar surfactants can be used such as sodium lauryl sulfate and other non-ionic surfactants.

In addition to the calcium and phosphate salts and the optional ingredients mentioned hereinabove, the solid products of this invention may also contain at least one flavoring agent and/or at least one sweetening agent.

Examples of suitable flavoring agents include, for example, oil of wintergreen, oil of peppermint, oil of spearmint, oil of sassafras, and oil of clove.

Suitable sweetening agents include, e.g., saccharin, dextrose, levulose, sodium cyclamate, and aspartame. Mixtures of sugar with a sweetener, e.g., sucralose, are also contemplated for use in the present invention.

As mentioned previously herein, the solid products of this invention may be in the form of chewing gum, lozenges, candies, edible food products, tablets and the like. In preferred embodiments, the solid products of this invention are in the form of chewing gum products. Chewing gums are the preferred vehicles for delivering the cationic and anionic components of the present invention because the inherent nature of chewing gums allows prolonged contact with the teeth and, further, because the gum base can provide sustained release of the anionic and cationic components of the products of this invention, thus minimizing the amount of the anionic and cationic components that must-be used.

Chewing gum products within the scope of this invention may be any of a variety of different chewing gums, bubble gums, dragees, and the like, including low or high moisture, sugar or sugarless, wax-containing or wax-free, low calorie (via high base or low calorie bulking agents), and/or may contain other dental health agents.

Chewing gum generally consists of a water-insoluble gum base, a water-soluble portion and flavors. The water-soluble portion dissipates with a portion of the flavor over a period of time during chewing. The gum base portion is retained in the mouth throughout the chew.

The insoluble gum base generally contains elastomers, resins, fats and oils, softeners, and inorganic fillers. The gum base may or may not include wax. The insoluble gum base can constitute from about 5% to about 95%, preferably from about 10% to about 50%, more preferably from about 20% to about 35%, by weight of the chewing gum.

In one embodiment, the chewing gum base which can be used in the present invention contains from about 20% to about 60% by weight of a synthetic elastomer, from 0% to about 30% by weight of a natural elastomer, from about 5% to about 55% by weight of an elastomer plasticizer, from about 4% to about 35% by weight of a filler, from about 5% to about 35% by weight of a softener, and, optionally, minor amounts (about it by weight or less) of miscellaneous ingredients such as colorants, antioxidants, and the like.

Synthetic elastomers suitable for use herein include but are not limited to polyisobutylene with GPC weight average molecular weight of from about 10,000 to about 95,000, preferably from about 50,000 to about 80,000; isobutylene-isoprene copolymer (butyl elastomer); styrene-butadiene copolymers having styrene-butadiene ratios of from about 1:3 to about 3:1, preferably from about 1:1 to about 1:3; polyvinyl acetate having a GPC weight average molecular weight of from about 2000 to about 90,000, preferably from about 10,000 to about 65,000; polyisoprene; polyethylene; vinyl acetate-vinyl laurate copolymer having a vinyl lauryl content of from about 5% to about 50% by weight, preferably from about 10% to about 45% by weight, of the copolymer, and combinations thereof.

Non-limiting examples of suitable natural elastomers include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. Preferred natural elastomers include jelutong, chicle, sorva, and massaranduba balata.

The preferred concentrations of the synthetic elastomer and the natural elastomer will vary depending on whether the chewing gum in which the base is used is adhesive or conventional, bubble gum or regular gum, as discussed below.

Non-limiting examples of suitable elastomer plasticizers include natural rosin esters such as glycerol esters of partially hydrogenated rosin, glycerol esters polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomers will also vary depending on the specific application, and on the type of elastomer which is used.

Non-limiting examples of suitable fillers/texturizers include magnesium and calcium carbonate; ground limestone; silicate types such as magnesium and aluminum silicate; clay; alumina; talc; titanium oxide; mono-, di- and tri-calcium phosphate; cellulose polymers, such as wood; and combinations thereof.

Non-limiting examples of suitable softeners/emulsifiers include tallow; hydrogenated tallow; hydrogenated and partially hydrogenated vegetable oils; cocoa butter; glycerol monostearate; glycerol triacetate; lecithin; mono-, di-, and triglycerides; acetylated monoglycerides; fatty acids such as stearic acid, palmitic acid, oleic acid and linoleic acid; and combinations thereof.

Suitable colorants and whiteners include, e.g., FD&C-type dyes and lakes, fruit and vegetable extracts, titanium dioxide and combinations thereof.

The base may or may not include wax.

In addition to a water-insoluble gum base portion, a typical chewing gum product includes a water-soluble bulk portion and one or more flavoring agents. The water-soluble portion can include, e.g., bulk sweeteners, high intensity sweeteners, flavoring agents, softeners, emulsifiers, colors, acidulants, fillers, antioxidants, and other components that provide desired attributes.

Softeners are added to chewing gum products to optimize the chewability and mouth feel of the gum. The softeners, which are also known as plasticizers and plasticizing agents, generally constitute from about 0.5% to about 15% by weight of the chewing gum. The softeners may include, e.g., glycerin, lecithin, and combinations thereof. Aqueous sweetener solutions such as those containing sorbitol, hydrogenated starch hydrolysates, corn syrup and combinations thereof, may also be used as softeners and binding agents in chewing gum products.

Bulk sweeteners include both sugar and sugarless components. The bulk sweetener(s) preferably constitutes from about 5% to about 95% by weight, more preferably from about 20% to about 80% by weight, and most preferably from about 30% to about 60% by weight, of the chewing gum.

Sugar sweeteners generally include saccharide-containing components such as, e.g., sucrose, dextrose, maltose, dextrin, dried invert sugar, fructose, levulose, galactose, corn syrup solids, and the like, alone or in combination. sugarless sweeteners include, e.g., sugar alcohols such as sorbitol, mannitol, xylitol, hydrogenated starch hydrolysates, maltol, and the like, alone or in combination.

High intensity artificial sweeteners can also be used, alone or in combination with the above. Non-limiting examples of such sweeteners include sucralose, aspartame, salts of acesulfame, alitame, saccharin and its salts, cyclamic acid and its salts, glycyrrhizin, dihydrochalccones, thaumatin, monellin, and the like, alone or in combination. To provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

The amount of the artificial sweetener used will vary greatly and will depend on such factors as potency of the sweetener, rate of release, desired sweetness of the product, level and type of flavor used, and cost considerations. Thus, the active level of the artificial sweetener may vary from about 0.02% to about 8.0% by weight. When carriers used for encapsulation are included, the amount of the encapsulated sweetener used will be proportionately higher.

Combinations of sugar and/or sugarless sweeteners may be used in the chewing gum product of this invention. Additionally, the softener may also provide additional sweetness such as with aqueous sugar or alditol solutions.

If a low calorie gum is desired, a low caloric bulking agent can be used. Non-limiting examples of such low calorie bulking agents include polydextrose, raftilose, raftilin, fructooligosaccharides, palatinose oligosaccharides, guar gum hydrolysates, or indigestible dextrin.

Suitable flavoring agents include those which have been previously described herein.

The flavoring agent can be used in the chewing gum of this invention in an amount preferably ranging from about 0.1% to about 15.0% by weight, more preferably from about 0.2% to about 5.0% by weight.

The chewing gum may be either sugarless or sugar-containing. Preferably, the chewing gum is sugar-containing so as to overcome some of the sensory quality problems of sugarless gums, as well as the problem of gastrointestinal disturbances caused in some chewers by the sugar alcohols used in sugarless gums.

The chewing gum may also contain a dental abrasive. Dental abrasives are particularly valuable in chewing gums because of the polishing action which occurs during chewing. The term "dental abrasives" as used herein includes all manner and form of such materials which are normally used in toothpastes, chewing gums and the like. The preferred dental abrasive for use in this invention is dicalcium diphosphate dihydrate, which also serves as an alkaline buffer. Other non-limiting examples of suitable dental abrasives include calcium carbonate, sodium metaphosphate, aluminum hydroxide, magnesium carbonate, calcium sulphate, silicas such as aerogels and xerogels, and tricalcium phosphate. The dental abrasive is preferably used in an amount of from about 1.0% to about 30.0% by weight, more preferably from about 1.5% to about 20.0% by weight.

The chewing gum of this invention may also contain glycerine, which serves to soften and maintain the chewability of the chewing gum for prolonged periods and also adds to the sweetness of the chewing gum. The glycerine is preferably used in an amount of from about 0.01% to about 10.0% by weight, more preferably from about 0.2% to about 5.0% by weight of the chewing gum.

A typical process for preparing chewing gum products is as follows. The gum base is melted at a temperature of from about 85° C. to about 90° C., cooled to about 78° C., and placed in a pre-warmed (60° C.) standard mixing kettle equipped with sigma blades. The emulsifier is then added. .Next, a portion of the sorbitol and the glycerin is added and mixed for an additional 3 to 6 minutes. The mixing kettle is cooled and mannitol and the remainder of the sorbitol and glycerin are then added and mixing is continued. At this time, the unflavored chewing gum has a temperature of from about 39° C. to about 42° C. Flavor oil is then added and incorporated into the base and the mixing is. continued.

Finally, the sweetener material is added and mixed for an additional 1 to about 10 minutes. The remineralization system is added as the last ingredient. The final gum temperature is from about 39° C. to about 43° C. The chewing gum product is then discharged from the kettle, rolled, scored and formed into chewing gum pieces.

What is claimed is:

1. A chewing gum for remineralizing subsurface lesions and/or for mineralizing exposed dentin tubles in teeth, comprising:

(a) a cationic component comprising at least one partially water-soluble calcium salt;

(b) an anionic component comprised of at least one water-soluble phosphate salt; and (c) a separating component for separating said components (a) and (b), said separating component comprising a water-insoluble gum base, said gum base being capable of releasing said components (a) and (b) into water and/or saliva when said chewing gum is mixed with said water and/or saliva;

wherein said components (a) and (b) have a pH in water such that a mixed aqueous composition formed by mixing said components (a) and (b) with said water and/or saliva has a pH of from about 4.0 to about 10.0;

further wherein said cationic component comprises an amount of said calcium salt such that in said mixed aqueous composition a first portion of said calcium salt exists as dissolved calcium cations and a second portion of said calcium salt exists as undissolved calcium salt, said anionic component comprising an amount of said phosphate salt such that said mixed aqueous composition further comprises dissolved phosphate anions released by said phosphate salt.

2. A chewing gum according to claim 1, wherein the amount of said calcium salt in said cationic component is such that said mixed aqueous composition comprises no more than about 1,400 ppm of said dissolved calcium cations and at least about 500 ppm of said dissolved calcium salt.

3. A chewing gum according to claim 1, wherein the amount of said calcium salt in said cationic component is such that said mixed aqueous composition comprises from about 100 ppm to about 800 ppm of said dissolved calcium cations and at least about 500 ppm of said undissolved calcium salt.

4. A chewing gum according to claim 1, wherein the amount of said phosphate salt in said anionic component is such that said mixed aqueous composition comprises at least about 100 ppm of said dissolved phosphate anions.

5. A chewing gum according to claim 1, wherein the amount of said calcium salt in said cationic component is such that said mixed aqueous composition comprises no more than about 1,400 ppm of said dissolved calcium cations and at least about 500 ppm of said undissolved calcium salt, further wherein the amount of said phosphate salt in said anionic component is such that said mixed aqueous comprises at least about 100 ppm of said dissolved phosphate anions.

6. A chewing gum according to claim 1, wherein said components (a) and (b) have a pH in water such that said mixed aqueous composition has a pH of from greater than about 4.0 to about 7.0.

7. A chewing gum according to claim 1, wherein said components (a) and (b) have a pH in water such that said mixed aqueous composition has a pH of from about 4.5 to about 6.5.

8. A chewing gum according to claim 1, wherein said components (a) and (b) have a pH in water such that said mixed aqueous composition has a pH of from about 5.00 to about 5.75.

9. A chewing gum according to claim 1, wherein said calcium salt is selected from the group consisting of calcium sulfate, anhydrous calcium sulfate hemihydrate, calcium sulfate dihydrate, calcium malate, calcium tartrate, calcium malonate and calcium succinate.

10. A chewing gum according to claim 1, wherein said calcium salt is calcium sulfate.

11. A chewing gum according to claim 1, wherein said cationic component further comprises at least one non-toxic, water-soluble salt of a divalent metal other than calcium in an amount such that said mixed aqueous composition further comprises dissolved divalent metal cations.

12. A chewing gum according to claim 1, wherein said divalent metal is selected from the group consisting of magnesium, tin, strontium and zinc.

13. A chewing gum according to claim 11, wherein the amount of said divalent metal salt in said cationic component is such that said mixed aqueous composition comprises at least about 100 ppm of said dissolved divalent metal cations.

14. A chewing gum according to claim 1, further comprising a stabilizing agent.

15. A chewing gum according to claim 14, wherein said stabilizing agent is selected from the group consisting of a desiccating agent and an encapsulating coating disposed on one or both of said cationic and anionic components, said encapsulating coating readily dissolving, dispersing or emulsifying in saliva.

16. A chewing gum according to claim 1, wherein said cationic component further comprises at least one water-soluble salt of a metal other than calcium, wherein said metal salt comprises an anion which is identical to an anion of said calcium salt.

17. A chewing gum according to claim 1, wherein said product is capable of simultaneously releasing said anionic and cationic components into said water and/or said saliva.

* * * * *

UNITED STATES PATENT AND TRADEMARK OFFICE
CERTIFICATE OF CORRECTION

PATENT NO. : 6,451,290 B2
DATED : September 17, 2002
INVENTOR(S) : Anthony E. Winston et al.

It is certified that error appears in the above-identified patent and that said Letters Patent is hereby corrected as shown below:

Column 22,
Line 39, change "dissolved" to -- undissolved --.

Signed and Sealed this

Tenth Day of December, 2002

JAMES E. ROGAN
*Director of the United States Patent and Trademark Office*